(12) United States Patent
Al-Qaoud et al.

(10) Patent No.: US 8,877,980 B2
(45) Date of Patent: Nov. 4, 2014

(54) PHENYLBORONIC ACID

(75) Inventors: Khaled Mahmood Al-Qaoud, Amman (JO); Penelope Ahmad Shihab, Amman (JO); Luay Fawzi Abu-Qatouseh, Amman (JO); Christopher R. Lowe, Cambridge (GB); Abdel Monem Mohammad Rawashdeh, Amman (JO); Yusuf Abdalsalam Alkhayyat, Amman (JO); Samer Sami Ratrout, Amman (JO); Saleem Muneer Naser, Amman (JO)

(73) Assignee: Al-Urdonia Lemudaddat Al-Ajsam Co., Amman (JO)

( * ) Notice: Subject to any disclaimer, the term of this patent is extended or adjusted under 35 U.S.C. 154(b) by 0 days.

(21) Appl. No.: 13/609,347

(22) Filed: Sep. 11, 2012

(65) Prior Publication Data

US 2014/0073603 A1    Mar. 13, 2014

(51) Int. Cl.
| | |
|---|---|
| *C07F 5/02* | (2006.01) |
| *C07F 9/02* | (2006.01) |
| *A01N 55/08* | (2006.01) |
| *A61K 31/69* | (2006.01) |

(52) U.S. Cl.
USPC .............................. 568/1; 514/64

(58) Field of Classification Search
CPC ........ C07F 5/025; C07F 5/027; C07C 233/01
USPC .................................. 568/1; 564/211; 514/64
See application file for complete search history.

(56) References Cited

PUBLICATIONS

Morissette et al. "High-throughput crystallization: polymorphs, salts, co-crystals and solvates of pharmaceutical solids" Advanced Drug Delivery Reviews, 2004, vol. 56, pp. 275-300.*

* cited by examiner

*Primary Examiner* — Kendra D Carter
(74) *Attorney, Agent, or Firm* — Renner, Otto, Boisselle & Sklar, LLP

(57) ABSTRACT

The present invention relates to a specific phenylboronic acid compound having anti-cancer, anti-inflammatory, and anti-microbial activity, in addition to a pharmaceutical composition comprising the same. The present invention also discloses a process for preparing said compound. The compound is represented by the formula (I):

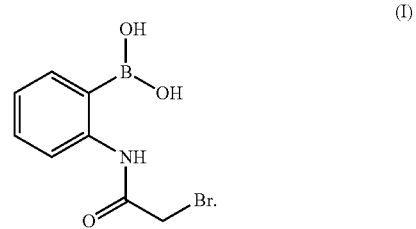

2 Claims, 1 Drawing Sheet

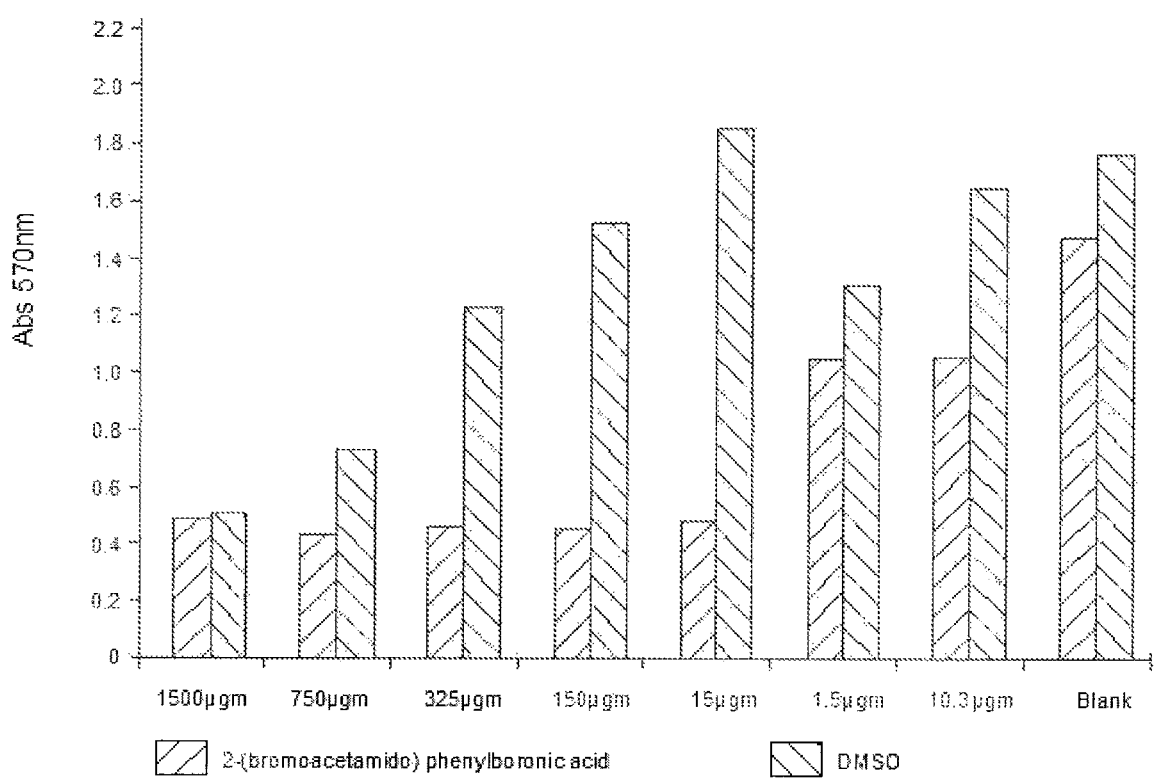

PHENYLBORONIC ACID

FIELD OF THE INVENTION

The invention is directed to a specific phenylboronic acid compound, specifically to the phenyboronic's use in human or veterinary therapeutics for treating diseases or conditions in a mammal, preferably a human, which are ameliorated or alleviated by the modulation, preferably inhibition, of a condition mediated by proteasome.

BACKGROUND OF THE INVENTION

Cancer is one of the main causes of death in the world. Although significant efforts have been made to find new approaches for treating cancer, the primary treatment options remain surgery, chemotherapy and radiation therapy, either alone or in combination. Surgery and radiation therapy, however, are generally useful only for defined types of cancer. Chemotherapy is the method that is generally useful in treating patients with metastatic cancer or diffuse cancers, such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused by microorganisms are becoming increasingly difficult to treat and cure. Particularly, more and more microorganisms are developing resistance to current antimicrobial agents.

Furthermore, a growing number of diseases are classified as inflammatory diseases. Such diseases include conditions such as asthma. These diseases continue to affect larger and larger numbers of people worldwide, despite new therapies and medical advances.

Proteasome inhibitors (PIs) are a proven class of therapeutic agents in the treatment of cancers including multiple myeloma (MM), Waldenstr öm macroglobulinemia, and mantle cell lymphoma. These proteasome inhibitors have also showed promise in treating autoimmune diseases in animal models. For example, studies in mice bearing human skin grafts found a reduction in the size of lesions from psoriasis after treatment with a proteasome inhibitor. These inhibitors also showed positive effects in rodent models of asthma. In addition proteasome inhibitors have shown promising results in treating microbial infections.

Proteasome inhibitors (PIs) are chemically classified into boronates, beta-lactams, epoxyketones, and peptide amides. Boronic acid and ester compounds hold particular promise as inhibitors of the proteasome and display a variety of pharmaceutically useful biological activities.

DESCRIPTION OF THE RELATED ART

A need exists for additional anti-cancers, anti-microbial, and anti-inflammatory agents to treat cancer, inflammatory diseases and infectious disease. Continuous efforts are being made to identify new potentially useful anti-cancer, anti-inflammatory, and anti-microbial agents.

Thus, Numerous boronic acid compounds and compositions for the treatment of various diseases are disclosed in the prior art. Among these compounds, boronic ester and acid compounds useful as proteasome inhibitors and their use to reduce the rate of muscle protein degradation, to reduce the activity of NF-kappa B in a cell, to reduce the rate of degradation of p53 protein in a cell, to inhibit cyclin degradation in a cell, to inhibit the growth of a cancer cell, and to inhibit NF-kappa B dependent cell adhesion.

In addition, certain boronic acid compounds inhibit the growth of cancer cells are disclosed in the prior art.

also, the prior art discloses peptide boronic acid compounds that inhibit fibroblast activating protein.

SUMMARY OF THE INVENTION

It is an object of the present invention to eliminate the disadvantages of the prior art by providing a novel compound represented by the formula (I):

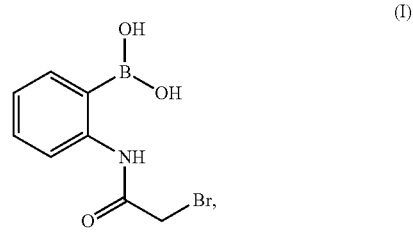 [SMILES: O=C(CBr)Nc1ccccc1B(O)O]

(I)

or a pharmaceutically acceptable salt thereof.

The compound of the invention is preferably a phenylboronic acid derivative. The compound preferably has anti-cancer, anti-inflammatory and anti-microbial activity. This compound is preferably 2-(bromoacetamido)phenylboronic acid, or a pharmaceutically acceptable salt thereof.

A second object of the present invention, is to provide anti-cancer, anti-inflammatory, and anti-microbial pharmaceutical compositions comprising the compound, or pharmaceutically acceptable salts thereof.

There is also provided a pharmaceutical composition comprising the compound, or a pharmaceutically acceptable salt and a pharmaceutically acceptable carrier, excipient or additive. Preferably, the compound is present in the composition in an amount effective to inhibit the proteasome function in a mammal.

The present invention also relates to a process for preparing the compound or a pharmaceutically acceptable salt thereof, comprising the reaction of a compound of Formula (II):

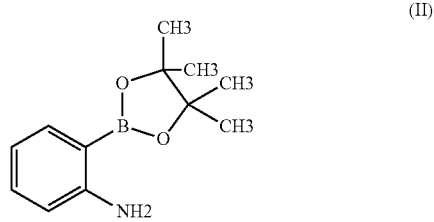 [SMILES: CC1(C)OB(c2ccccc2N)OC1(C)C]

(II)

with a compound of formula (III):

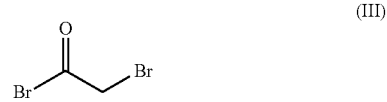

(III)

to form a compound of Formula (IV)

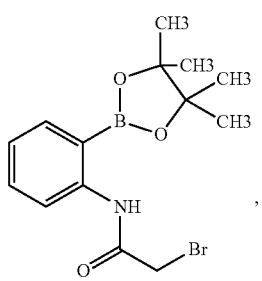

and de-protecting the compound of Formula (IV) by acidic/basic media to form compound of Formula (I).

Another object of the present invention, is to provide a method of inhibiting conditions mediated by proteasome in a patient in need of this inhibiting, comprising administering to the patient an effective amount of the compound. Therefore, there is provided a method for inhibiting a condition selected from the group consisting of growth of a cell cancer,
rate of muscle protein degradation in a cell,
activity of NF-kappa B,
rate of intracellular protein breakdown,
rate of degradation of p53 protein in a cell,
cyclin degradation in a cell,
an inflammatory condition,
antigen presentation in a cell,
inducible NF-kappa B,
HIV replication, and
microbial infection
in a patient, the method comprising administering to said patient an effective amount a compound of Formula (I):

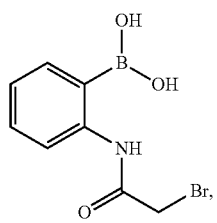

, or a pharmaceutically acceptable salt thereof.

Preferably, the patient is diagnosed with, or at risk of developing, a condition selected from the group consisting of tissue rejection, organ rejection, arthritis, microbial infection, dermatoses, inflammatory bowel disease, asthma, osteoporosis, osteoarthritis, and an autoimmune disease.

the compound, or a pharmaceutically acceptable solvate thereof, is preferably for use in a medicament for the treatment of tissue rejection in a mammal.

The compound, or a pharmaceutically acceptable solvate thereof, is also for use in a medicament for the treatment of organ rejection in a mammal.

The compound, or a pharmaceutically acceptable solvate thereof is also for use in a medicament for the treatment of arthritis in a mammal.

The compound, or a pharmaceutically acceptable solvate thereof, is also for use in a medicament for the treatment of microbial infection in a mammal.

The compound, or a pharmaceutically acceptable solvate thereof, is also for use in a medicament for the treatment of dermatoses in a mammal.

The compound, or a pharmaceutically acceptable solvate thereof, is also for use in a medicament for the treatment of inflammatory bowel disease in a mammal.

The compound, or a pharmaceutically acceptable solvate thereof, is also for use in a medicament for the treatment of asthma in a mammal.

The compound, or a pharmaceutically acceptable solvate thereof, is also for use in a medicament for the treatment of osteoporosis in a mammal.

The compound, or a pharmaceutically acceptable solvate thereof, is also for use in a medicament for the treatment of osteoarthritis in a mammal.

The compound or a pharmaceutically acceptable solvate thereof, is also for use in a medicament for the treatment of an autoimmune disease in a mammal.

The compound, or a pharmaceutically acceptable solvate thereof, is also for use in a medicament for the treatment of cancer in a mammal.

BRIEF DISCRIPTION OF THE DRAWINGS

FIG. 1 shows cytotoxic effect of 2-(bromoacetamido)phenylboronic acid on CHO cell line as determined by MTT assay.

DETAILED DESCRIPTION OF THE INVENTION

A first aspect of the present invention is directed to a novel boronic acid compound having the formula (I)

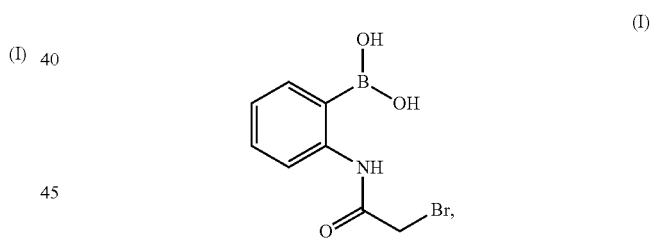

or a pharmaceutically acceptable salt thereof.

The compound represents a phenylboronic acid derivative, which is 2-(bromoacetamido)phenylboronic acid or a pharmaceutically acceptable salts thereof.

The compound is prepared by reacting a compound of Formula (II):

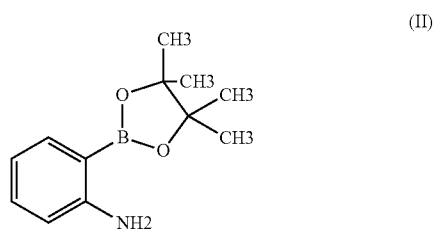 [SMILES: CC1(C)OB(c2ccccc2N)OC1(C)C]

with a compound of Formula (III):

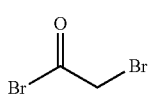
(III)

to produce a compound of Formula (IV)

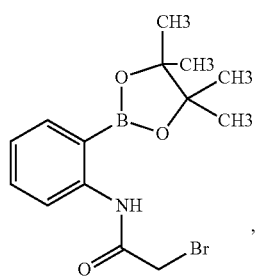
(IV)

and then de-protecting the compound of Formula (IV) by acidic/basic media to produce the compound of Formula (I).

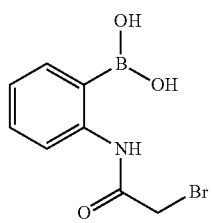
(I)

Another aspect of the present invention lies in, that boronic acid and ester derivatives, in general, as well as isosteric variations thereof, inhibit proteasome function. Thus, the present invention also relates to the use of the compound of formula (I) for reducing the rate of proteasome dependent intracellular protein breakdown, such as reducing the rate of muscle protein degradation, reducing the rate of degradation of p53 protein, inhibiting cyclin degradation, and for inhibiting the activity of NF-kappa B in a cell.

The present invention relates to the use of the compound of formula (I) for treating specific conditions in animals that are mediated or exacerbated, directly or indirectly, by proteasome functions. These conditions comprise inflammatory conditions, such as tissue rejection, organ rejection arthritis, infection, dermatoses, inflammatory bowel disease, asthma, osteoporosis, osteoarthritis and autoimmune disease such as lupus and multiple sclerosis. The compound of formula (I) is used for treating cell proliferative diseases, such as cancer, psoriasis and restenosis, and accelerated muscle protein breakdown that accompanies various physiological and pathological states and is responsible to a large extent for the loss of muscle mass (atrophy) that follows nerve injury, fasting, fever, acidosis, and certain endocrinopathies. On the other hand, it has been found that the compound of formula (I) inhibits the growth of a variety of pathogenic bacterial, viral, and fungal strains, for example, *E. coli, p. aeruginosa*, and methicillin-resistant *staphylococcus aureus* (MRSA).

In another aspect, the invention provides pharmaceutical compositions comprising the compound of formula (I) in an amount effective to inhibit proteasome function in a mammal, or a pharmaceutically acceptable salt, and a pharmaceutically acceptable carrier or diluent. If a pharmaceutically acceptable salt of the compound of the invention is utilized in these compositions, the salt preferably is derived from an inorganic or organic acid or base.

The term "pharmaceutically acceptable carrier" is used herein to refer to a material that is compatible with a recipient subject, preferably a mammal, more preferably a human, and is suitable for delivering an active agent to the target site without terminating the activity of the compound. The toxicity or adverse effects, if any associated with the carrier preferably are commensurate with a reasonable risk/benefit ratio for the intended use of the compound.

The terms "carrier", "adjuvant", or "vehicle" are used interchangeably herein, and include any and all solvents, diluents, and other liquid vehicles, dispersion or suspension aids, surface active agents, pH modifiers, isotonic agents, thickening or emulsifying agents, preservatives, solid binders, lubricants and the like, as suited to the particular dosage form desired. Except insofar as any conventional carrier medium is incompatible with the compound of the invention, such as by producing any undesirable biological effect or otherwise interacting in a deleterious manner with any other component(s) of the pharmaceutically acceptable composition, its use is contemplated to be within the scope of this invention. Coloring agents, releasing agents, coating agents, sweetening, flavoring and perfuming agents, preservatives and antioxidants can also be present in the composition.

The pharmaceutical compositions can be manufactured by methods well known in the art such as conventional granulating, mixing, dissolving, encapsulating, lyophilizing, or emulsifying processes, among others. The compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions.

The pharmaceutical compositions are formulated for pharmaceutical administration to a mammal, preferably a human being. These pharmaceutical compositions may be administered orally, parenterally, by inhalation spray, topically, rectally, nasally, buccally, vaginally or via an implanted reservoir. The formulations of the invention may be designed to be short-acting, fast-releasing, or long-acting. Still further, The compound can be administered in a local rather than systemic means, such as administration (e.g., by injection) at a target site.

The pharmaceutical compositions preferably are formulated for administration to a patient having at risk of developing, or experiencing a recurrence of a proteasome-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of the compound are well within the bounds of routine experimentation and therefore, well within the scope of the instant invention. The pharmaceutical compositions may further comprise another therapeutic agent, such other therapeutic agent is one that is normally administered to patients with the disease or condition being treated.

The invention will be further described and illustrated in the following examples.

EXAMPLES

The following examples illustrate the present invention without, however, limiting the same thereto.

Example 1

Synthesis of 2-(bromoacetamido)phenylboronic acid intermediate (50 g, 0.228 mol) of 2-aminophenyl boronic acid pinacol ester and (110 g, 0.798 mole) of potassium carbonate were charged into 10 L, 3 necks RBF connected with overhead stirrer, thermometer and additional funnel, 5 L of Chloroform, synthetic grade was loaded then stirred for 10±5 minutes at 25±5° C. after that (115 g, 50 mL, 0.57 mol) of Bromoacetyl bromide was added drop wise during 10±5 minutes while the mixture stirred. After end of loading, the mixture was stirred for 1-2 hrs at 25±5° C., the reaction completion was monitored by TLC (Ethyl acetate:n-hexane, 15:85 v/v). Afterward, 4-5 L of purified water was loaded then transferred to 10 L separatory funnel and steeled down for 10 minutes, chloroform layer (lower) was separated and dried over 50 g of sodium sulfate and filtered. The filtrate solution was concentrated under vacuum to dryness. The residue was recrystallized from diethyl ether to get pure 2-(bromoacetamido)phenylboronic acid intermediate, the product was characterized by $^1$H-NMR, $^{13}$C-NMR, mass and elemental analysis.

Example 2

Synthesis of 2-(bromoacetamido)phenylboronic acid 45 g of 2-(bromoacetamido)phenylboronic acid intermediate was charged into 3-neck RBF connected with thermometer, overhead stirrer and reflux condenser. 2.25 L of chloroform was added and the mixture stirred for 10±5 minutes at 25±5° C., after that (27±1 g, 2.08 eq.) of sulfuric acid was added dropwise. The reaction mixture solution was stirred and heated to reach temperature content at 55-60° C. then stirred at that temperature for 4±1 his the reaction progress, was followed by TIC (Ethyl acetate:n-hexane, 15:85 v/v) where a violet solution obtained, after reaction completion, a gummy material obtained at the bottom with yellow to orange color the supernatant (violet solution) was removed off and the remaining gummy residue was dissolved in 900±100 mL Acetone. After getting clear solution, a 1 L of purified water was added dropwise over 15±5 minutes. The suspension was stirred and cooled to 0-5° C. then stirred for about 1 hrs at 0-5° C., filtered and white solid filtered was washed with 100 mL acetone. The wet powder was dried under vacuum in oven at 50±5° C. to get pure 2-(bromoacetamido)phenylboronic acid compound. The quality of obtained product was checked by $^1$H-NMR, $^{13}$C-NMR, mass and elemental analysis.

Antimicrobial Susceptibility Testing of 2-(bromoacetamido)phenylboronic Acid

Example 3

Bacterial Strains and Growth Conditions

The following bacterial strains were used; *S. aureus* ATCC 29350, *E. coli* ATCC 8739, and *P. aeruginosa* ATCC 27853. The cultivation medium for *P. aeruginosa* and *E. coli* were tryptone soy Agar (Oxoid, UK), and, 5% defibrinated sheep blood added to columbia blood agar base (Oxoid, UK). The bacterial cultures were aerobically grown at 37° C. for 24 hrs. For antimicrobial testing, the bacterial cultures were prepared by picking colonies from logarithmic phase of growth and suspended in 5 ml of Mueller Hinton broth with suitable supplements. The bacterium inoculum sizes were adjusted to $10^8$ CFU/ml for all strains.

Example 4

Preparation of Standard Solutions of 2-(bromoacetamido)phenylboronic Acid, Vancomycin and Penicillin Standard Stock solutions of 2-(bromoacetamido)phenylboronic acid were prepared by gradually dissolving 2-(bromoacetamido)phenylboronic acid to the maximum solubility in 100% DMSO (1 mg/ml). Similarly standard stock solution of Vancomycin and Penicillin (1 mg/ml) were used as positive controls.

Antimicrobial Susceptibility Testing and (Minimum Inhibitory Concentration) MIC Determination

Example 5

Disk Diffusion

For the disk diffusion assay, bacterial suspensions were prepared to the standard McFarland's (0.5) and subsequently uniformly spread on a solid growth medium in a Petri dish. Sterile paper disks (6 mm in diameter; oxoid, UK) were placed on the surface of each agar plate and were impregnated with 30 µL to a final concentration of 600 ug/ml of each agent to be tested. The plates were incubated for the recommended time periods (18-24 hrs) under appropriate cultivation conditions. Antibacterial activity was determined by measuring an inhibition zone around a disk following the incubation. Disks impregnated with sterile distilled water, DMSO served as negative controls and disks with standard antibiotics Vancomycin and penicillin (Oxoid, UK) served as positive controls. Triplicates at each concentration were performed and the average of the results was taken.

Example 6

Broth Microdilution

For the broth microdilution test, 100 µL of each bacterial suspension in suitable growth medium was added to the wells of a sterile 96-well microtitre plate already containing 100 µL of two-fold serially diluted 2-(bromoacetamido)phenylboronic acid or vancomycin and penicillin in proper growth medium. The final volume in each well was 200 µL. Control wells were prepared with culture medium, bacterial suspension only compound only and DMSO in amounts corresponding to the highest quantity present. The contents of each well were mixed on a microplate shaker (Lab.companion, Korea,) at 200 rpm for 2 min prior to incubation for 24 h in the cultivation conditions described above. The MIC was the lowest concentration where no viability was observed after 24 h on the basis of metabolic activity. To indicate cell viability, the presence of a purple color was determined after adding 20 µL/well of 500 ug/ml MTT (3-(4,5-Dimethylthiazol-2-yl-2, 5-diphenyltetrazolium bromide, Sigma) and incubated under appropriate cultivation conditions (37° C. for 3 hrs). To determine the formation of formazan by living cells, $OD_{570}$ was measured by a Microplate Reader (Thermoscientific, Finland) after adding 200 μL/well of a solubilizing solution (a mixture of DMSO:ethanol (1:1)). Positive controls were wells with a bacterial suspension in an appropriate growth medium. Negative controls were wells with growth medium and antimicrobial compound. All measurements of MIC values were repeated in triplicate.

2000 rpm for 10 minutes, then the supernatant was aspirated and the formazan crystals were dissolved by adding 200 μl of 11 ethanol/DMSO solvent. Colour development was measured at 570 nm using a microplate reader (Stat Fax® 2100 Microplate Reader, Awareness Technology Inc., Palm City, Fla., USA).

TABLE (I)

Results of Antimicrobial activity testing of 2-(bromoacetamido) phenylboronic acid against both Gram positive and Gram negative bacteria

| | Antimicrobial effect vs. Bacterial species | | | | | | | |
|---|---|---|---|---|---|---|---|---|
| | S. aureus ATCC 2592 | | MRSA clinical strain | | E. coli ATCC 8739 | | P. aerugionsa ATCC 27853 | |
| antimicrobial Agent | Zone of inhibition (mm) | MIC (μg/ml) | Zone of inhibition (mm) | MIC (μg/ml) | Zone of inhibition (mm) | MIC (μg/ml) | Zone of inhibition (mm) | MIC (μg/ml) |
| Vancomycin (100 μg/ml) | 22 (S) | 0.4 | 22 (S) | 0.4 | NP | NP | NP | NP |
| Ampicillin (20 mg/ml) | NP | NP | NP | NP | 36 (S) | 25 | 16 (R) | 150 |
| 2-(bromoacetamido) phenyl boronic acid (600 μg/ml) | 24 | 1.56 | 24 | 1.56 | 16 | 75 | 0 | >600 |

S = sensitive
R = resistant
MRSA = methicillin resistant S. aureus
MIC = minimal inhibitory concentration
NP = not performed Example 7

Anti-Cancer Activity Testing

Chinese hamster ovary cancer cell line (CHO), carcinoma tissue from the human larynx (HEp-2), and breast cancer MDA-MB-438 were purchased from the ECACC European Collection of Cell Cultures (Salisbury, Wiltshire, UK). Both Cell lines were maintained as exponentially growing cultures in DMEM culture medium supplemented with 10% fetal bovine serum and 2 Mm glutamine (PAA Laboratories GmbH, Pasching, Austria). Cell lines were cultured at 37° C. in air/carbon dioxide (95/5) atmosphere and 95% humidity. The cells were trypsinised upon reaching confluence, washed, counted by trypan blue exclusion test, and seeded in 96 well plates ($20 \times 10^3$/well). After 24 hours, the chemical compound 2-(bromoacetamido)phenylboronic acid was added at the following concentrations: 0, 0.3, 1.5, 15, 150, 375, 750, and 1500 microgram/ml. The solvent (DMSO) was used as control to assess its toxicity. The zero concentration served as the negative control. The cells were incubated with the extract for 48 hours and then the MTT assay was performed.

Example 8

MTT (3{4,5-dimethylthiazol-2-yl}-2,5-diphenyltetrazolium bromide) assay

The media on the cells were aspirated and the cells were washed twice with sterile PBS buffer. 100 μl of fresh complete DMEM medium was added to each well in addition to 10 μl of 5 mg/ml MTT solution (Sigma, St. Louis, Mo., USA). After 3-hour incubation at 37° C., the plate was centrifuged at Example 9

Single Dose Acute Toxicity Study and LD50 Determination

Results of Acute Toxicity of 2-(bromoacetamido)phenylboronic Acid in Balb/c Mice
  a. Control group did not show any deaths or behavioral changes.
  b. All tested mice behaved normally post 2-bromoacetamido)phenylboronic acid administration at 10, 50 and 100 mg/kg. No death or any clinical signs appeared and all mice showed normal activity and neuromuscular coordinations.
  c. Reduced activity was observed in all mice treated with 150 and 200 mg/kg 2-(bromoacetamido)phenylboronic acid. This effect started 30 minutes post treatment. The activity was recovered after 3 hours post treatment (for survived animals). However, animals that did not survive showed a clear apnea, loss of appetite, loss of muscle coordination, and righting reflex followed by immobility and death.
  d. The time of deaths was observed as dose dependent. Mice treated with 150 mg/kg died within 18 hours of 2-(bromoacetamido)phenylboronic acid administration while mice treated with 200 mg/kg died within 4 hours post treatment.
  e. Gross autopsy for dead mice and all mice that survived (at day 14) did not reveal any significant findings.
  f. No significant change in the body weights was seen in all groups.

It was concluded in this example that acute oral administration of 2-(bromoacetamido)phenylboronic acid molecule dissolved in DMSO to BALB/c mice showed systemic toxicity and caused death at doses above 100 mg/kg. However, a curve generated LD50 of 2-(bromoacetamido)phenylboronic acid molecule was estimated in the vicinity of 130 mg/kg.

TABLE (II)

Single Dose Acute Toxicity Study and LD50 Determination Findings

| Group (Dose) | Gender | Mouse Number | % Death/gender | % Death/group |
|---|---|---|---|---|
| Control (DMSO alone) | Males | 5 | 0 | 0 |
|  | Females | 5 | 0 |  |
| 2-(bromoacetamido) phenylboronic acid (10 mg/kg) | Males | 5 | 0 | 0 |
|  | Females | 5 | 0 |  |
| 2-(bromoacetamido) phenylboronic acid (50 mg/kg) | Males | 5 | 0 | 0 |
|  | Females | 5 | 0 |  |
| 2-(bromoacetamido) phenylboronic acid (100 mg/kg) | Males | 5 | 0 | 0 |
|  | Females | 5 | 0 |  |
| 2-(bromoacetamido) phenylboronic acid (150 mg/kg) | Males | 5 | 40% | 70% |
|  | Females | 5 | 100% |  |
| 2-(bromoacetamido) phenylboronic acid (200 mg/kg) | Males | 5 | 80% | 70% |

While the present invention has been described in details and with reference to specific embodiments thereof, it will be apparent to one skilled in the art that various, additions, omissions and modifications can be made without departing from the spirit and scope thereof.

The invention claimed is:
1. A compound of the Formula (I):

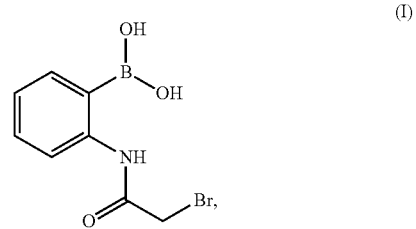 [SMILES: O=C(CBr)Nc1ccccc1B(O)O]

or a pharmaceutically acceptable salt thereof.
2. The compound of claim 1, wherein said compound is 2-(bromoacetamido)phenylboronic acid.

* * * * *